US012774421B2

(12) United States Patent
Maadasamy Durai et al.

(10) Patent No.: US 12,774,421 B2
(45) Date of Patent: Oct. 27, 2026

(54) PROCESS FOR CRACKING TO LIGHT OLEFINS WITH ISOMERIZATION AND/OR OLIGOMERIZATION

(71) Applicant: UOP LLC, Des Plaines, IL (US)

(72) Inventors: Sakthivelan Maadasamy Durai, Gurugram (IN); Ling Zhou, Palatine, IL (US); Jan de Ren, Arlington Heights, IL (US); Xi Zhao, Arlington Heights, IL (US)

(73) Assignee: UOP LLC, Rosemont, IL (US)

( * ) Notice: Subject to any disclaimer, the term of this patent is extended or adjusted under 35 U.S.C. 154(b) by 150 days.

(21) Appl. No.: 18/945,032

(22) Filed: Nov. 12, 2024

(65) Prior Publication Data

US 2025/0207044 A1 Jun. 26, 2025

Related U.S. Application Data

(60) Provisional application No. 63/614,347, filed on Dec. 22, 2023.

(51) Int. Cl.

| | |
|---|---|
| ***C10G 57/02*** | (2006.01) |
| ***C07C 2/02*** | (2006.01) |
| ***C07C 2/04*** | (2006.01) |
| ***C07C 2/06*** | (2006.01) |
| ***C07C 2/08*** | (2006.01) |

(Continued)

(52) U.S. Cl.
CPC ................ *C10G 57/02* (2013.01); *C07C 2/02* (2013.01); *C07C 2/04* (2013.01); *C07C 2/06* (2013.01); *C07C 2/08* (2013.01); *C07C 4/02* (2013.01); *C07C 4/06* (2013.01); *C10G 2300/1081* (2013.01); *C10G 2400/20* (2013.01); *C10G 2400/22* (2013.01)

(58) Field of Classification Search
CPC ............ C10G 57/02; C10G 2300/1081; C10G 2400/20; C10G 2400/22; C10G 11/18; C10G 50/00; C07C 2/02; C07C 2/04; C07C 2/06; C07C 2/08; C07C 4/02; C07C 4/06
See application file for complete search history.

(56) References Cited

U.S. PATENT DOCUMENTS

| | | | | |
|---|---|---|---|---|
| 4,788,366 A * | 11/1988 | Harandi | C07C 2/00 | 585/314 |
| 9,434,892 B2 * | 9/2016 | Pradeep | C10G 51/026 | |
| 9,670,425 B2 * | 6/2017 | Vanden Bussche | C10G 50/00 | |

(Continued)

*Primary Examiner* — Ali Z Fadhel
(74) *Attorney, Agent, or Firm* — Paschall & Associates, LLC; James C. Paschall

(57) ABSTRACT

We have discovered a process for catalytic production of olefins comprising passing a feed stream to an isomerization unit to provide a first hydrocarbon stream rich in iso-paraffins. The first hydrocarbon stream is contacted with a first stream of fluid catalyst in a first reactor riser to produce a first mixture of spent catalyst and product gases. The first mixture of spent catalyst and product gases is separated into a first cracked product stream and a first stream of cool catalyst. A dilute ethylene stream is separated from the first cracked product stream which is oligomerized to produce a second hydrocarbon stream comprising C4+ oligomers. The second hydrocarbon stream is contacted with a second stream of fluid catalyst in a second reactor riser to produce a second mixture of spent catalyst and product gases.

20 Claims, 1 Drawing Sheet

(51) Int. Cl.
*C07C 4/02* (2006.01)
*C07C 4/06* (2006.01)

(56) References Cited

U.S. PATENT DOCUMENTS

| | | | | |
|---|---|---|---|---|
| 9,777,228 | B2 * | 10/2017 | Davydov | C10G 51/06 |
| 10,077,218 | B2 * | 9/2018 | Feugnet | C10G 57/02 |
| 2005/0121361 | A1 * | 6/2005 | Duplan | C10G 69/126 208/78 |
| 2007/0129586 | A1 * | 6/2007 | Zimmermann | C10G 35/14 422/600 |
| 2010/0158767 | A1 * | 6/2010 | Mehlberg | C10G 11/18 422/139 |
| 2011/0108458 | A1 * | 5/2011 | Leonard | C10G 11/18 208/113 |
| 2011/0245567 | A1 * | 10/2011 | da Silva Ferreira Alves | C07C 2/24 585/518 |
| 2015/0166433 | A1 * | 6/2015 | Luebke | C10G 11/18 585/653 |
| 2015/0376090 | A1 * | 12/2015 | Mehlberg | C10G 35/00 585/329 |

* cited by examiner

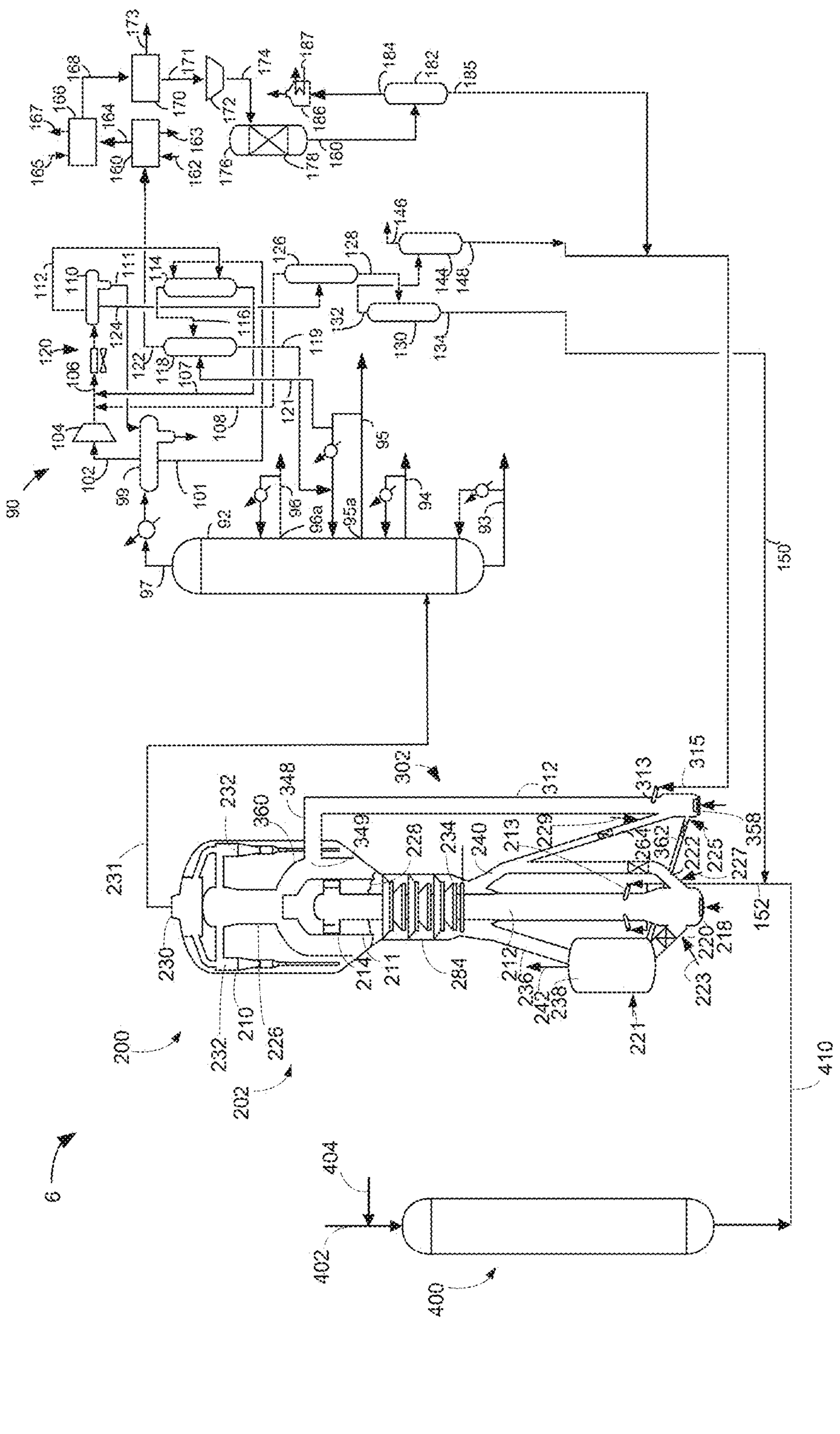

PROCESS FOR CRACKING TO LIGHT OLEFINS WITH ISOMERIZATION AND/OR OLIGOMERIZATION

FIELD

The field is the reaction of feed with fluid catalyst. The field particularly relates to an FCC process to produce light olefins with a dual reactor system.

BACKGROUND

Catalytic cracking can create a variety of products from larger hydrocarbons. Often, a feed of a heavier hydrocarbon, such as a vacuum gas oil, is provided to a catalytic cracking reactor, such as a fluid catalytic cracking (FCC) reactor. Various products may be produced from an FCC unit, including a gasoline product and/or light product such as propylene and/or ethylene.

In FCC systems, a single reactor or a dual reactor can be utilized. Although additional capital costs may be incurred by using a dual reactor system, one of the reactors can be operated to tailor conditions for maximizing products, such as light olefins including propylene and/or ethylene.

It can often be advantageous to maximize yield of a product in one of the reactors and minimize dry gas formation. Additionally, there may be a desire to maximize the production of a product from one reactor that can be recycled back to the other reactor to produce a desired product, such as propylene.

Thus, there can be a desire to provide an efficient reactor process for catalytic cracking for maximizing propylene product and minimizing dry gas formation.

BRIEF SUMMARY

We have discovered a process for catalytic production of olefins comprising passing a feed stream to an isomerization unit to provide a first hydrocarbon stream rich in iso-paraffins. The first hydrocarbon stream is contacted with a first stream of fluid catalyst in a first reactor riser to produce a first mixture of spent catalyst and product gases. The first mixture of spent catalyst and product gases is separated into a first cracked product stream and a first stream of cool catalyst. A dilute ethylene stream is separated from the first cracked product stream which is oligomerized to produce a second hydrocarbon stream comprising C4+ oligomers. The second hydrocarbon stream is contacted with a second stream of fluid catalyst in a second reactor riser to produce a second mixture of spent catalyst and product gases.

BRIEF DESCRIPTION OF THE DRAWING

The FIGURE is a sectional, elevational of the process and apparatus of the present disclosure.

Definitions

The term "downstream communication" means that at least a portion of fluid flowing to the subject in downstream communication may operatively flow from the object with which it fluidly communicates.

The term "upstream communication" means that at least a portion of the fluid flowing from the subject in upstream communication may operatively flow to the object with which it fluidly communicates.

The term "direct communication" means that fluid flow from the upstream component enters the downstream component without passing through any other intervening vessel.

The term "indirect communication" means that fluid flow from the upstream component enters the downstream component after passing through an intervening vessel.

The term "bypass" means that the object is out of downstream communication with a bypassing subject at least to the extent of bypassing.

As used herein, "naphtha" or "full range naphtha" refers to a hydrocarbon mixture having a 10 percent point below 175° C. (347° F.) and a 95 percent point below 240° C. (464° F.) as determined by distillation in accordance with the standard method of ASTM D86; "light naphtha" to a naphtha fraction with a boiling range within the range of C4 to 166° C. (330° F.); and "heavy naphtha" to a naphtha fraction with a boiling range within the range of 166° C. (330° F.) to 211° C. (412° F.).

As used herein, the term "rich" can mean an amount of at least generally about 50%, and preferably about 70%, by mole, of a compound or class of compounds in a stream.

As used herein, the term "paraffinic" in reference to a feed or stream refers to a light hydrocarbon mixture comprising at least 80 weight percent paraffins, no more than 10 weight percent aromatics, and no more than 40 weight percent cycloparaffins.

As used herein, the term "mixed $C_4$'s" in reference to a feed or stream refers to a light hydrocarbon mixture comprising at least 90 weight percent of hydrocarbon compounds having 4 carbon atoms.

As used herein, the term "predominant" or "predominate" means greater than 50%, suitably greater than 75% and preferably greater than 90%.

The term "column" means a distillation column or columns for separating one or more components of different volatilities. Unless otherwise indicated, each column includes a condenser on an overhead of the column to condense and reflux a portion of an overhead stream back to the top of the column and a reboiler at a bottom of the column to vaporize and send a portion of a bottoms stream back to the bottom of the column. Feeds to the columns may be preheated. The top pressure is the pressure of the overhead vapor at the vapor outlet of the column. The bottom temperature is the liquid bottom outlet temperature. Overhead lines and bottoms lines refer to the net lines from the column downstream of any reflux or reboil to the column. Stripper columns may omit a reboiler at a bottom of the column and instead provide heating requirements and separation impetus from a fluidized inert media such as steam. Stripping columns typically feed a top tray and take main product from the bottom.

As used herein, the term "separator" means a vessel which has an inlet and at least an overhead vapor outlet and a bottoms liquid outlet and may also have an aqueous stream outlet from a boot. A flash drum is a type of separator which may be in downstream communication with a separator that may be operated at higher pressure.

DETAILED DESCRIPTION

We have found that charging an iso-paraffin rich stream to a catalytic cracking reactor results in greater conversion and yield of propylene. We propose to isomerize the hydrocarbon feedstock to provide the favorable reaction feed to the FCC reactor to maximize the yield of propylene.

Now turning to the FIGURE, wherein like numerals designate like components, a process and apparatus generally include an isomerization unit 400, a FCC unit 6 and a product recovery section 90. The FCC unit section 6 includes a first FCC reactor 200 comprising a first FCC reactor unit 202.

A first hydrocarbon feedstock stream in line 402 may comprise $C_4$-$C_{10}$ hydrocarbons. Preferably, the first hydrocarbon feedstock stream comprises light naphtha, such as $C_5$-$C_7$ hydrocarbons. The first hydrocarbon feedstock stream may comprise at least about 50 wt % paraffins, suitably at least about 60 wt % paraffins and preferably at least about 70 wt % paraffins. The first hydrocarbon feedstock stream may comprise no more than about 25 wt % olefins, suitably no more than about 15 wt % olefins and preferably no more than about 1 wt % olefins. The first hydrocarbon feedstock stream may be predominant in normal-paraffins.

In an embodiment, the first hydrocarbon feedstock stream in line 402 is a paraffin-rich naphtha stream that is isomerized in an isomerization unit 400, under isomerization conditions, in the presence of hydrogen stream in line 404 to produce an isomerization reactor effluent. The isomerization reactor effluent is an iso-paraffin rich hydrocarbon stream in line 410 which is then sent to the first reactor riser 212.

Hydrogen is admixed with or remains with the isomerization feed to the isomerization unit to provide a mole ratio of hydrogen to hydrocarbon feed of about 0.01 to 20. The hydrogen may be supplied totally from outside the process or supplemented by hydrogen recycled to the feed after separation from isomerization reactor effluent. Light hydrocarbons and small amounts of inerts such as nitrogen and argon may be present in the hydrogen. Water should be removed from hydrogen supplied from outside the process, preferably by an adsorption system as is known in the art.

The isomerization of the paraffin-rich naphtha stream in line 402 can be accomplished in any manner known in the art or by using any suitable catalyst known in the art. One or more beds of catalyst may be used within the reactor(s). It is preferred that the isomerization be operated in a co-current mode of operation. Fixed bed, trickle bed down flow or fixed bed liquid filled up-flow modes are both suitable. See also, for example, WO2023129920A1, which discloses a suitable catalyst may include chlorided alumina, sulfated zirconia, tungstated zirconia or zeolite-containing isomerization catalysts. The higher isomerization catalyst may be amorphous, e.g., based upon amorphous alumina, or zeolitic. A zeolitic catalyst would still normally contain an amorphous binder. The catalyst may comprise a sulfated zirconia and platinum as described in U.S. Pat. No. 5,036,035 and European Patent Application 0666109 A1 or a platinum group metal on chlorided alumina as described in U.S. Pat. Nos. 5,705,730 and 6,214,764. Another suitable catalyst is described in U.S. Pat. No. 5,922,639. U.S. Pat. No. 6,818,589 discloses a catalyst comprising a tungstated support of an oxide or hydroxide of a Group IVB (IUPAC 4) metal, preferably zirconium oxide or hydroxide, at least a first component which is a lanthanide element and/or yttrium component, and at least a second component being a platinum-group metal component.

Isomerization conditions may include a temperature between 40 to 250° C. (104 to 482° F.) and a pressure between 100 kPa absolute (14 psia) to 10,000 kPa absolute (1450 psia). In another embodiment the isomerization conditions include a temperature between 150 to 220° C. (302 to 428° F.) and a pressure between 3102 kPa absolute (450 psia) to 3792 kPa absolute (550 psia). The Liquid hourly space velocities (LHSV) range from 0.2 to 25 volumes of hydrocarbon feed per hour per volume of catalyst. Other operating conditions for the isomerization zone are well known in the art. The isomerized product may be continuously withdrawn. In an embodiment unreacted paraffins may be separated from the isoparaffins in the reactor effluent, by conventional means, such as fractional distillation or adsorption, while the unreacted normal paraffins may be recycled to the isomerization reactor as a portion of the first hydrocarbon feedstock stream in line 402.

The FIGURE shows the first FCC reactor unit 202 comprising a first reactor riser 212 and a first reactor vessel 210. The first FCC reactor unit 202 includes the first reactor riser 212 in which a first hydrocarbon stream in line 152 through a distributor 213 or more distributors near the base of the first reactor riser 212 is contacted with a first stream of fluid catalyst.

The first hydrocarbon stream in line 152 may be provided by a mixture of C5+ hydrocarbon stream in line 150 obtained from the product recovery section 90 and the iso-paraffin rich hydrocarbon stream in line 410. The first hydrocarbon stream in line 152 is predominantly isoparaffinic, so it will be more easily crack and crack more selective to olefins. Process conditions in the first reactor riser 212 may include a cracking reaction temperature of about 400° to about 650° C., preferably about 538° C. to about 650° C. at the reactor outlet. Cracking occurs at an absolute pressure between about 100 kPa (14 psia) to about 650 kPa (94 psia), preferably between about 140 kPa (20 psia) to about 450 kPa (65 psia). A steam flow rate of about 5 to about 25 wt % of the first hydrocarbon stream is added to the first reactor riser 212. Control valves on a first hot catalyst pipe 220 and on a first recycle catalyst pipe 222 can be used to adjust the catalyst density in the first reactor riser 212 thus enabling control of the space velocity therein.

The catalyst can be a single catalyst or a mixture of different catalysts. Usually, the catalyst includes two components or catalysts, namely a first component or catalyst, and a second component or catalyst. Such a catalyst mixture is disclosed in, e.g., U.S. Pat. No. 7,312,370 B2. Generally, the first component may include any of the well-known catalysts that are used in the art of FCC, such as an active amorphous clay-type catalyst and/or a high activity, crystalline molecular sieve. Zeolites may be used as molecular sieves in FCC processes. Preferably, the first component includes a large pore zeolite, such as a Y-type zeolite, an active alumina material, a binder material, including either silica or alumina, and an inert filler such as kaolin.

Typically, the zeolitic molecular sieves appropriate for the first component have a large average pore size. Usually, molecular sieves with a large pore size have pores with openings of greater than about 0.7 nm in effective diameter defined by greater than about 10, and typically about 12, member rings. Pore Size Indices of large pores can be above about 31. Suitable large pore zeolite components may include synthetic zeolites such as X and Y zeolites, mordenite and faujasite. A portion of the first component, such as the zeolite, can have any suitable amount of a rare earth metal or rare earth metal oxide.

The second component may include a medium or smaller pore zeolite catalyst, such as a MFI zeolite, as exemplified by at least one of ZSM-5, ZSM-11, ZSM-12, ZSM-23, ZSM-35, ZSM-38, ZSM-48, and other similar materials. Other suitable medium or smaller pore zeolites include ferrierite, and erionite. Preferably, the second component is a medium or small pore zeolite dispersed on a matrix including a binder material such as silica or alumina and an inert filler material such as kaolin. The second component may also include some other active material such as Beta zeolite. These compositions may have a crystalline zeolite content of about 10 to about 50 wt % or more, and a matrix material content of about 50 to about 90 wt %. Components containing about 40 wt % crystalline zeolite material are preferred, and those with greater crystalline zeolite content may be used. Generally, medium and smaller pore zeolites are characterized by having an effective pore opening diameter of less than or equal to about 0.7 nm, rings of about 10 or fewer members, and a Pore Size Index of less than about 31.

The total catalyst mixture in the first FCC reactor 200 may contain about 1 to about 100 wt % of the second component, namely a medium to small pore crystalline zeolite, with greater than or equal to about 30 wt % of the second component being preferred. The first component may comprise the balance of the catalyst composition. In some preferred embodiments, the relative proportions of the first and second components in the mixture may not substantially vary throughout the first FCC reactor 200. The high concentration of the medium or small pore zeolite as the second component of the catalyst mixture can improve selectivity to light olefins. In one exemplary embodiment, the second component can be a ZSM-5 zeolite catalyst and the catalyst mixture can include about 4 to about 50 wt % ZSM-5 zeolite excluding any other components, such as binder and/or filler.

Preferably, at least one of the first and/or second catalysts is an MFI zeolite have a silicon to aluminum ratio greater than about 15, preferably greater than about 75. In one exemplary embodiment, the silicon to aluminum ratio can be about 15:1 to about 35:1.

The contacting may occur in the narrow first reactor riser 212, extending upwardly to the bottom of the first reactor vessel 210. The first stream of fluid catalyst may be fluidized with steam distributed from a distributor 218 at a bottom of the first reactor riser 212. The first stream of fluid catalyst may be provided by a mixture of a first stream of hot catalyst from the first hot catalyst pipe 220 and a first stream of recycle catalyst from the first recycle catalyst pipe 222. The heat from the catalyst vaporizes the first hydrocarbon feedstock, and the first hydrocarbon feedstock is thereafter cracked to the first cracked product stream of lighter molecular weight in the presence of the first catalyst stream as both are transferred up the first reactor riser 212 into the first reactor vessel 210 providing a first mixture of spent catalyst and product gases.

The first reactor riser 212 terminates in an upper end of a first disengagement chamber 211 located within the first reactor vessel 210 at a curved duct 214 or a plurality thereof. The curved duct 214 may centrifugally discharge a first mixture of spent catalyst and product gases into the first disengagement chamber 211. By centrifugal discharge, the first mixture is discharged from inwardly to outwardly. Centrifugal discharge of gases and catalyst produces a swirling helical pattern about the interior of the first disengagement chamber 211 to effect disengagement of the first mixture of spent catalyst and product gases into the first cracked product stream and a first stream of cool catalyst in the first disengagement chamber 211.

The first stream of cool catalyst collects in a dense catalyst bed 228. The first stream of product gas passes upwardly through a gas recovery conduit 226, is further separated from catalyst in cyclones 232 and is discharged from the first reactor vessel 210 through a product outlet 230 in a product line 231 as a gaseous FCC hot product stream.

The FIGURE illustrates a second FCC reactor unit 302 in which a second hydrocarbon stream in line 315 distributed through a distributor 313 or more distributors near the base of the second reactor riser 312 is contacted with a second stream of fluid catalyst in the second riser. In an embodiment, the second FCC reactor unit 302 is integrated with the first FCC reactor unit 202. However, the second FCC reactor unit 302 may stand alone from the first FCC reactor 202 in its own FCC reactor.

The second hydrocarbon feedstock may be predominant in olefins. The second hydrocarbon stream is more olefinic than said first hydrocarbon stream. The second hydrocarbon stream may comprise at least about 20 wt % olefins, suitably at least about 40 wt % olefins and preferably at least about 60 wt % olefins. The second hydrocarbon stream may comprise at least 1 wt % paraffins, suitably at least about 15 wt % paraffins and preferably at least about 25 wt % paraffins. The second hydrocarbon stream comprises a $C_4$ hydrocarbons recovered from the product recovery section 90 and a $C_4$+ oligomer stream. The second hydrocarbon stream may further comprise once cracked $C_5$ to $C_7$ hydrocarbons from the product gases of the first riser.

The second stream of fluid catalyst may have the same catalyst composition as the first stream of catalyst. In another preferred embodiment, the second stream of fluid catalyst can predominantly comprise the second component and in a further embodiment can contain only the second component, preferably a ZSM-5 zeolite, as the catalyst.

The second stream of fluid catalyst may be fluidized with steam distributed from a distributor 358 at a bottom of the second reactor riser 312. The second stream of fluid catalyst may be provided by a mixture of a second stream of hot catalyst from a second hot catalyst pipe 362 and a second stream of recycle catalyst from a second recycle catalyst pipe 264. The second hydrocarbon feedstock vaporizes and converts or cracks to a second cracked product stream comprising ethylene and propylene in greater concentration than in the second hydrocarbon stream. Molar expansion and vaporization causes the second hydrocarbon stream and the second cracked product stream to rapidly ascend the second reactor riser 312 entraining the second stream of fluid catalyst as a second mixture of spent catalyst and product gas.

Process conditions in the second reactor riser 312 may be less severe than in the first reactor riser 212. The second reactor riser 312 may operate at one or more of the following conditions relative to the first reactor riser 212: a lower outlet temperature, a lower residence time and a lower catalyst density than the first riser. Hydrocarbon partial pressure can also be varied for adjusting the second reactor riser severity. Hydrocarbon partial pressure may be varied by adjusting total pressure in the second reactor riser 312 independent of the pressure in the first FCC reactor 202 and perhaps adjusting the steam rate to the second reactor riser 312.

Conditions in the second reactor riser 312 may include a cracking reaction temperature of about 400° C. to about 600° C., preferably about 565° C. to about 600° C. at the reactor outlet. The cracking occurs at an absolute pressure between about 100 kPa (14 psia) to about 506 kPa (74 psia), preferably between about 138 kPa (20 psia) to about 310 kPa (45 psia). Steam of about 5 to about 25 wt % of second hydrocarbon stream rate is added to the second reactor riser 312. Control valves on the second hot catalyst pipe 362 and on the second recycle catalyst pipe 264 can be used to adjust the catalyst density in the second reactor riser 312 thus enabling control of the space velocity therein.

The second reactor riser 312 of the second FCC reactor unit 302 may be located externally to the first FCC reactor

202 but share the first reactor vessel 210 with the first reactor riser 212 and the first FCC reactor 202. The second reactor riser 312 comprises a discharge opening 349 in a second disengagement chamber 360. The second disengagement chamber 360 contains the discharge opening 349 of the second reactor riser 312. The second disengagement chamber 360 may be in the first reactor vessel 210. In an embodiment, a horizontal transfer line 348 of the second reactor riser 312 terminates in the second disengagement chamber 360. The discharge opening 349 of the second reactor riser 312 may tangentially discharge the second mixture of spent catalyst and product gas into the second disengagement chamber 360. In other embodiments, the horizontal transfer line 348 may be exchanged for an alternative connector such a T-type connector or an elbow with a more acute or more obtuse angle. Tangential discharge of the second mixture of spent catalyst and product gas through the discharge opening 349 from the second reactor riser 312 produces a swirling helical pattern about the interior of the second disengagement chamber 360. The disengagement of the second mixture of spent catalyst and product gas into a second stream of cool catalyst and a second cracked product stream may be conducted outwardly and concentrically of the disengagement of the first mixture of catalyst and product gas into the first cracked product stream and the first stream of cool catalyst. It is important that the first mixture of catalyst and product gas does not mix with the second mixture of catalyst and product gas until the bulk of the catalyst is removed from the product gas to maximize selectivity to propylene.

In an embodiment, the second stream of cool catalyst collects in the dense catalyst bed 228 along with the first stream of cool catalyst. In a further embodiment, the second cracked product stream passes upwardly through the gas recovery conduit 226 along with the first cracked product stream, is further separated from catalyst in cyclones 232 and is discharged from the first reactor vessel 210 through the product outlet 230 in the product line 231 as the gaseous FCC hot product stream.

A mixed stream of disengaged cool catalyst from the dense catalyst bed 228 passes downwardly through a stripping section 284. A stripping fluid, typically steam enters a lower portion of stripping section 284 through a distributor 234. Countercurrent contact of the catalyst with the stripping fluid through a series of stripping baffles, packing or grates displaces product gases from the catalyst as it continues downwardly through the stripping section 284.

A first stream of stripped catalyst from the stripping section 284 passes through a heater conduit 236 to a catalyst heater 238. The catalyst heater 238 provides the first stream of hot catalyst in the first hot catalyst pipe 220 that is fed to the first reactor riser 212 and the second stream of hot catalyst in the second hot catalyst pipe 362 that is fed to the second reactor riser 312.

A second stream of stripped catalyst from the dense catalyst bed 228 passes in a recycle conduit 240 to provide the first stream of recycle catalyst in the first recycle catalyst pipe 222 to the first reactor riser 212 and the second stream of recycle catalyst in the second recycle catalyst pipe 264 to the second reactor riser 312. The catalyst in the first FCC reactor unit 202 and second FCC reactor unit 302 does not coke up as much. Hence, insufficient coke can be burned to balance heat demands in the reactors. To supplement heat to the first FCC reactor 202 and the second FCC reactor unit 302, gaseous or liquid fuel (not shown in the FIGURE) is fired to heat the catalyst. Catalyst from the first FCC reactor unit 202 and the second FCC reactor unit 302 may be delivered to the catalyst heater 238 by the heater conduit 236.

A portion of the first stream of fluid catalyst gets heated in the catalyst heater 238 before contacting the first stream of fluid catalyst with the first hydrocarbon stream. A portion of the second stream of fluid catalyst gets heated in the catalyst heater 238 before contacting the second stream of fluid catalyst with the second hydrocarbon feedstock stream. A flue gas stream in line 242 generated out of the catalyst heater 238 may be appropriately routed to the flue gas treatment unit. In another embodiment, the fuel firing in the catalyst heater 238 may be replaced by electrical coils powered by renewable or fossil fuel-based electricity.

To generate more coke on catalyst, a $C_4$+ hydrocarbon stream may be fed to the catalyst heater 238 in a first coking line 221 directly to catalyst in the catalyst heater 238 or one or more of a second coking line 223 to the first stream of hot catalyst in the first hot catalyst pipe 220, a third coking line 225 to the second stream of hot catalyst in the second hot catalyst pipe 362, a fourth coking line 227 to the recycle catalyst in the first recycle catalyst pipe 222, and a fifth coking line 229 to the recycle catalyst in the second recycle catalyst pipe 264. The $C_4$+ injection in the catalyst pipes will help optimize the coke level in the catalyst which maximizes propylene selectivity in first and second risers. $C_4$+ hydrocarbon injections should be located downstream of the control valve in the catalyst pipes. The coke distribution in the catalyst shall be about 0.1 to about 5 wt % coke on catalyst, preferentially about 0.1 to about 2 wt % coke on catalyst in the first reactor riser 212, and about 0.1 to about 1 wt % coke on catalyst in the second reactor riser 312.

The product recovery section 90 is in downstream communication with the product outlet 230. "Communication" means that material flow is operatively permitted between enumerated components. In the product recovery section 90, the gaseous FCC hot product stream in the product line 231 is directed to a lower section of an FCC main fractionation column 92. The main column 92 is in downstream communication with the product outlet 230. Several fractions of FCC product may be separated and taken from the main column including a heavy slurry oil from the bottoms in line 93, a heavy cycle oil stream in line 94, a light cycle oil in line 95 taken from outlet **95*a* and a heavy naphtha stream in line 96 taken from outlet 96*a*. Any or all of lines 93-96 may be cooled and pumped back to the main column 92 to cool the main column typically at a higher location. Gasoline and gaseous light hydrocarbons are removed in overhead line 97 from the main column 92 and condensed before entering a main column receiver 99. The main column receiver 99 is in downstream communication with the product outlet 230, and the main column 92 is in upstream communication with the main column receiver 99**. "Upstream communication" means that at least a portion of the material flowing from the component in upstream communication may operatively flow to the component with which it communicates.

An aqueous stream is removed from a boot in the receiver 99. Moreover, a condensed light naphtha stream is removed in line 101 while an overhead stream is removed in line 102. The overhead stream in line 102 contains gaseous light hydrocarbon which may comprise a dilute ethylene stream. The streams in lines 101 and 102 may enter a vapor recovery section 120 of the product recovery section 90.

The vapor recovery section 120 is shown to be an absorption-based system, but any vapor recovery system may be used including a cold box system. To obtain sufficient separation of light gas components the gaseous stream in line 102 is compressed in compressor 104. More than one compressor stage may be used, but typically a dual stage compression is utilized. The compressed light hydrocarbon stream in line 106 is joined by streams in lines 107 and 108, chilled and delivered to a high-pressure receiver 110. An aqueous stream in line 111 from the receiver 110 may be routed to the main column receiver 99. A gaseous hydrocarbon stream in line 112 comprising the dilute ethylene stream is routed to a primary absorber 114 in which it is contacted with unstabilized gasoline from the main column receiver 99 in line 101 to effect a separation between $C_3^+$ and $C_2^-$ hydrocarbons. The primary absorber 114 is in downstream communication with the main column receiver 99. A liquid $C_3^+$ stream in line 107 is returned to line 106 prior to chilling. A primary off-gas stream in line 116 from the primary absorber 114 comprises the dilute ethylene stream for purposes of the present invention. However, to concentrate the ethylene stream further and to recover heavier components line 116 may optionally be directed to a secondary absorber 118, where a circulating stream of light cycle oil in line 121 diverted from line 95 absorbs most of the remaining $C_5^+$ and some $C_3$-$C_4$ material in the primary off-gas stream. The secondary absorber 118 is in downstream communication with the primary absorber 114. Light cycle oil from the bottom of the secondary absorber in line 119 richer in $C_3^+$ material is returned to the main column 92 via the pump-around for line 95. The overhead of the secondary absorber 118 comprising dry gas of predominantly $C_2^-$ hydrocarbons with hydrogen sulfide, ammonia, carbon oxides and hydrogen is removed in a secondary off-gas stream in line 122 to comprise a dilute ethylene stream.

Liquid from the high-pressure receiver 110 in line 124 is sent to a stripper 126. Most of the $C_2^-$ is removed in the overhead of the stripper 126 and returned to line 106 via overhead line 108. A liquid bottoms stream from the stripper 126 is sent to a first debutanizer column 130 in a bottoms line 128. The first debutanizer column 130 provides an overhead stream in line 132 comprising a $C_3$-$C_4$ hydrocarbon stream from the first debutanizer column. A bottoms stream in line 134 may comprise a debutanized naphtha stream. The debutanized naphtha stream comprising $C_5$+ paraffins is recycled in line 134 to be part of the first charge stock in line 152. The $C_3$-$C_4$ hydrocarbon stream taken in line 132 may be separated in a $C_3$-$C_4$ splitter column 144 into a $C_3$ hydrocarbon stream in an overhead line 146 and a $C_4$ hydrocarbon stream in a bottoms line 148. The $C_4$ hydrocarbon stream comprising olefinic $C_4$ hydrocarbons taken from a bottoms line 148 of the $C_3$-$C_4$ splitter column also in downstream communication with the main column 92 in line 97 may be recycled to the second FCC reactor unit 302 in the second hydrocarbon stream 315 as at least a portion of the second hydrocarbon stream The $C_3$ hydrocarbon stream in the overhead line 146 may be further processed for propylene recovery. The second hydrocarbon stream 315 may be preheated to a temperature of about 221° C. (400° F.) to about 621° C. (1150° F.) and charged to the second FCC reactor unit 302.

The dilute ethylene stream may be the secondary off-gas stream in line 122 may comprise an FCC dry gas stream comprising between about 5 and about 65 wt-% ethylene and preferably about 10 to about 55 wt-% ethylene. Methane will typically be the predominant component in the dilute ethylene stream at a concentration of between about 25 and about 55 wt-% with ethane being substantially present at typically between about 5 and about 45 wt-%. Between about 0.5 and about 25 wt-% and typically about 1 to about 20 wt-% of hydrogen and nitrogen each may be present in the dilute ethylene stream. Saturation levels of water may also be present in the dilute ethylene stream. If secondary absorber 118 is used, no more than about 5 wt-% of $C_3^+$ will be present with typically less than 0.5 wt-% propylene.

Besides hydrogen, other impurities such as hydrogen sulfide, ammonia, carbon oxides and acetylene may also be present in the dilute ethylene stream. Such impurities in a dry gas ethylene stream can poison an oligomerization catalyst. Hydrogen and carbon monoxide can reduce the metal sites to inactivity. Carbon dioxide and ammonia can attack acid sites on the catalyst. Hydrogen sulfide can attack metals on a catalyst to produce metal sulfides. Acetylene can polymerize and gum up on the catalyst or equipment.

The secondary off-gas stream in line 122, comprising a dilute ethylene stream may be introduced into an optional amine absorber unit 160 to remove hydrogen sulfide to lower concentrations. A lean aqueous amine solution, such as comprising monoethanol amine or diethanol amine, is introduced via line 162 into absorber 160 and is contacted with the flowing secondary off-gas stream to absorb hydrogen sulfide, and a rich aqueous amine absorption solution containing hydrogen sulfide is removed from absorption zone 160 via line 163 and recovered and perhaps further processed.

The amine-treated dilute ethylene stream in line 164 may be introduced into an optional water wash unit 166 to remove residual amine carried over from the amine absorber 160 and reduce the concentration of ammonia and carbon dioxide in the dilute ethylene stream in line 164. Water is introduced to the water wash in line 165. The water in line 165 is typically slightly acidified to enhance capture of basic molecules such as the amine. An aqueous stream in line 167 rich in amine and potentially ammonia and carbon dioxide leaves the water wash unit 166 and may be further processed.

In an aspect, the optionally amine treated dilute ethylene and perhaps water washed stream in line 168 may then be treated in an optional guard bed 170 to remove one or more of the impurities such as carbon monoxide, hydrogen sulfide and ammonia down to lower concentrations. The guard bed 170 may contain an adsorbent to adsorb impurities such as hydrogen sulfide that may poison an oligomerization catalyst. The guard bed 170 may contain multiple adsorbents for adsorbing more than one type of impurity. A typical adsorbent for adsorbing hydrogen sulfide is ADS-12, for adsorbing CO is ADS-106 and for adsorbing ammonia is UOP MOLSIV 3A, all available from UOP, LLC. The adsorbents may be mixed in a single bed or can be arranged in successive beds.

In another aspect, the optionally amine treated dilute ethylene and perhaps water washed stream in line 168 may be treated to recover or reduce hydrogen concentration in the dilute ethylene stream in line 168 to a lower level. In an exemplary embodiment, unit 170 is a pressure swing adsorption (PSA) unit instead of a guard bed. The optionally amine treated dilute ethylene and perhaps water washed stream in line 168 may be passed to a pressure swing adsorption (PSA) unit 170 to recover or reduce hydrogen concentration in the dilute ethylene stream in line 168 to a lower level. The optionally amine treated dilute ethylene and perhaps water washed stream in line 168 may enter the PSA 170 at a high pressure. The molecules heavier than hydrogen present in the optionally amine treated dilute ethylene and perhaps water washed stream in line 168 are adsorbed on the adsorbent while hydrogen molecules do not adsorb on the adsorbent and pass through the bed. The adsorbent may be selected from one or more of silica gel, alumina, activated carbon, molecular sieve including but not limited to zeolite, Metal Organic Framework (MOFs), etc. or their mixture. The PSA 170 may comprise a single layer or multi-layer bed of adsorbent of different composition. The light molecules such as hydrogen leave the PSA 170 at high pressure in line 173 and are recovered. The adsorbed heavy molecules are then desorbed and recovered at a lower pressure from the PSA 170 in a PSA tail gas stream comprising ethylene in line 171.

In an embodiment, the PSA unit 170 may be operated at an adsorption pressure of about 1500 kPa (220 psi) to 3500 kPa (515 psi), and a desorption pressure of about 100 kPa (15 psi) to about 300 kPa (44 psi).

In another aspect, the optionally amine treated dilute ethylene and perhaps water washed stream in line 168 may be passed through a membrane unit 170 to recover or reduce hydrogen concentration in the dilute ethylene stream in line 168 to a lower level. In the membrane unit 170, the optionally amine treated dilute ethylene and perhaps water washed stream in line 168 is passed through a membrane at a high pressure. In an exemplary embodiment, the membrane unit 170 may comprise a polyimide or a polyethersulfone-polyimide blend membrane. Other suitable membranes may include a polymer, porous ceramic, dense ceramic, or metallic membranes. After contact, the molecules heavier than hydrogen present in the optionally amine treated dilute ethylene and perhaps water washed stream in line 168 are mostly rejected by membrane as retentate. The heavy molecules comprising ethylene leave the membrane unit 170 at a high pressure and withdrawn in a retentate stream comprising ethylene in line 171 from the membrane unit 170. Hydrogen present in the optionally amine treated dilute ethylene and perhaps water washed stream in line 168 permeates through the membrane at higher selectivity than the retained molecules and the hydrogen is recovered at the other side of membrane at a lower pressure in a hydrogen stream in line 173.

The membrane unit 170 may be operated at a temperature of about 40° C. (104° F.) to about 80° C. (176° F.). The differential pressure across the membrane can be as low as about 70 kPa (10 psi) or as high as 14.5 MPa (2100 psi) depending on many factors such as the particular membrane used, the flow rate of the inlet stream and the availability of a compressor to compress the permeate stream if such compression is desired. In an embodiment, the differential pressure across the membrane may range between about 446 kPa (50 psig) and about 6996 kPa (1000 psig) feed pressure.

A dilute ethylene stream in line 171 perhaps amine treated, perhaps water washed and perhaps adsorption treated to remove more hydrogen sulfide, ammonia and carbon monoxide will typically have at least one of the following impurity concentrations: about 0.1 wt-% and up to about 5.0 wt-% of carbon monoxide and/or about 0.1 wt-% and up to about 5.0 wt-% of carbon dioxide, and/or at least about 1 wppm and up to about 500 wppm hydrogen sulfide and/or at least about 1 and up to about 500 wppm ammonia, and/or at least about 0.1 and up to about 10 wt-% hydrogen. The type of impurities present and their concentrations will vary depending on the processing and origin of the dilute ethylene stream.

Line 171 carries the dilute ethylene stream to a compressor 172 to be pressured up to reactor pressure. The compressor 172 is in downstream communication with the main column 92, the product recovery section 90, the product outlet 230. The compressed dilute ethylene stream can be compressed to at least about 3,550 kPa (500 psia) and perhaps no more than about 10,445 kPa (1500 psia) and suitably between about 4,930 kPa (700 psia) and about 7,687 kPa (1100 psia). It is preferred that the dilute ethylene stream be pressured up to above the critical pressure of ethylene which is about 4,992 kPa (724 psia) for pure ethylene to avoid rapid catalyst deactivation. The compressor 172 may comprise one or more stages with interstage cooling. A heater may be required to bring the compressed stream up to reaction temperature. The compressed dilute ethylene is carried in line 174 to an oligomerization reactor 176.

The oligomerization reactor 176 is in downstream communication with the compressor 172 and the primary and secondary absorbers 114 and 118, respectively. The oligomerization reactor preferably contains a fixed catalyst bed 178. The dilute ethylene feed stream contacts the catalyst preferably in a down flow operation. However, upflow operation may be suitable. The catalyst is preferably an amorphous silica-alumina base with a metal from Group 6, 8, 9 and 10 in the periodic table in the periodic table using IUPAC notations. In an aspect, the catalyst has a Group 8, 9, or 10 metal (hereinafter 8-10) promoted with a Group 6 metal. In an aspect, the catalyst may have a silica-to-alumina ratio of no more than 30 and preferably no more than 20. Typically, the silica and alumina will only be in the base, so the silica-to-alumina ratio will be the same for the catalyst as for the base. The metals can either be impregnated onto or ion exchanged with the silica-alumina base. Co-mulling is also contemplated. Additionally, a suitable catalyst will have a surface area of between about 50 and about 400 $m^2/g$ as determined by nitrogen BET.

A preferred oligomerization catalyst of the present invention has an amorphous silica-alumina base impregnated with 0.5-15 wt-% nickel in the form of 3.175 mm (0.125 inch) extrudates and a density of about 0.45 to about 0.65 g/mL. It is also contemplated that metals can be incorporated onto the support by other methods such as ion-exchange and co-mulling.

The dilute ethylene feed in line 174 may be contacted with the oligomerization catalyst in catalyst bed 178 at a temperature between about 100° and about 400° C. The reaction takes place predominantly in the gas phase at a GHSV 50 to 1000 $hr^{-1}$ on an ethylene basis. The conversion of ethylene in the feed stream to heavier hydrocarbons varies from at least about 40 wt-% and as much as about 75 wt-%. The ethylene will first oligomerize over the catalyst to heavier olefins. Some of the heavier olefins may cyclize over the catalyst, and the presence of hydrogen could facilitate conversion of the olefins to paraffins which are all heavier hydrocarbons than ethylene. However, the cyclized and saturated products are undesirable for cracking to propylene and shall be minimized by proper selection of catalyst and reaction conditions.

The catalyst may remain stable despite the impure feed, but it may be regenerated upon deactivation. Suitable regeneration conditions may include subjecting the catalyst, for example, in situ, to hot air at 500° C. for 3 hours. Activity and selectivity of the regenerated catalyst may be comparable to fresh catalyst.

An oligomerization product stream from the oligomerization reactor in line 180 can be transported to an oligomerization separation unit 182. The oligomerization separation unit may be a simple flash drum to separate a gaseous stream from a liquid stream. The oligomerization separation unit 182 is in downstream communication with the oligomerization reactor 176. A light raffinate stream in overhead line 184 comprising light gases such as hydrogen, methane, ethane, unreacted olefins and light impurities may be transported to a combustion unit 186 to generate steam in line 187. Alternatively, the light raffinate stream in overhead line 184 may be combusted in fire a heater (not shown) and/or to provide a source of flue gas to turn a gas turbine (not shown) to generate power. The overhead line 184 is in upstream communication with the combustion unit 186. A liquid bottoms stream in line 185 comprising $C_4$+ olefins, and preferably $C_4$ and $C_6$ olefins, may be further utilized for producing additional propylene.

The oligomerization liquid bottoms stream taken in line 185, comprising $C_4$+ olefins and other $C_2$ oligomers may be combined with the $C_4$ hydrocarbon stream in line 148 for recycle to the second FCC reactor unit 302 in the second hydrocarbon stream 315 as at least a portion of the second hydrocarbon stream. The second hydrocarbon stream will be richly olefinic and will crack to propylene molecules for recovery in line 146.

EXAMPLES

Example 1

A cracking catalyst was prepared by extruding MFI zeolite ($SiO_2/Al_2O_3$ molar ratio 400-500) with silica binder and steam the extrudate till its activity is attenuated to yield the following product at weight hourly space velocity (WHSV)=13.5 and Temperature=568° C., with a feed of 40 wt % mixed-butenes and 60 wt % mixed-butanes:

TABLE 1

| Ethylene | Propylene | Butene | Pentene | Butane | Pentane | Other/Heavy |
|---|---|---|---|---|---|---|
| 4.2 | 15.2 | 13.9 | 3.3 | 57.3 | 0.3 | 5.8 |

Example 2

The attenuated catalyst from Example 1 is used in cracking of two different $C_5$ hydrocarbon feeds, one rich in normal-pentane and the other rich in iso-pentane, at the same condition listed in Table 2 below. Applicants observed that the cracking product of iso-rich feed contains higher light olefin.

TABLE 2

| | Feed | |
|---|---|---|
| | 95 wt % n-$C_5$ 5 wt % $C_5$ olefins | 95 wt % i-$C_5$ 5 wt % $C_5$ olefins |
| Temp (° C.) | 600 | 593 |
| WHSV | 6.7 | 6.7 |
| Ethylene | 4.6 | 8.0 |
| Propylene | 12.8 | 15.0 |
| Butene | 6.1 | 10.4 |
| Pentene | 1.9 | 3.25 |
| Butane | 1.0 | 1.6 |
| Pentane | 49.3 | 48.3 |
| Other/Heavy | 24.3 | 13.4 |

Example 3

The attenuated catalyst from Example 1 is used in cracking of mixed $C_4$ feed (37.7 wt % iso-butane, 10.3 wt % n-butane, with the remaining being mixed linear $C_4$ olefins) at conditions listed in Table 3 below. Applicants observed that the conversion of n-butane is negligible while significant conversion of iso-butane could be observed.

TABLE 3

| Temp/ ° C. | WHSV | Conversion of n-butane (%) | Conversion of iso-butane (%) | Conversion of linear $C_4$ olefins (%) |
|---|---|---|---|---|
| 552.5 | 23.4 | ~0 | 1.4 | 75.9 |
| 572.5 | 23.4 | ~0 | 5.0 | 74.0 |
| 592.2 | 23.4 | ~0 | 9.4 | 72.1 |
| 591.6 | 11.9 | ~0 | 15.5 | 78.4 |

Specific Embodiments

While the following is described in conjunction with specific embodiments, it will be understood that this description is intended to illustrate and not limit the scope of the preceding description and the appended claims.

A first embodiment of the disclosure is a process for catalytic production of olefins comprising passing a feed stream to an isomerization unit to provide a first hydrocarbon stream rich in iso-paraffins; contacting a first hydrocarbon stream with a first stream of fluid catalyst in a first reactor riser to produce a first mixture of spent catalyst and product gases; separating the first mixture of spent catalyst and product gases into a first cracked product stream and a first stream of cool catalyst; separating a dilute ethylene stream from the first cracked product stream; oligomerizing the dilute ethylene stream to produce a second hydrocarbon stream comprising C4+ oligomers; and contacting the second hydrocarbon stream with a second stream of fluid catalyst in a second reactor riser to produce a second mixture of spent catalyst and product gases. An embodiment of the disclosure is one, any or all of prior embodiments in this paragraph up through the first embodiment in this paragraph wherein the first mixture of spent catalyst and product gases are separated in a first disengagement vessel and further comprising separating, in a second disengagement vessel, the second mixture of spent catalyst and product gases to provide a second cracked product stream and a second stream of cool catalyst. An embodiment of the disclosure is one, any or all of prior embodiments in this paragraph up through the first embodiment in this paragraph further comprising passing the first cracked product stream along with the second cracked product stream upwardly through a gas recovery conduit, and further separating from catalyst in a series of cyclones to produce a gaseous FCC hot product stream. An embodiment of the disclosure is one, any or all of prior embodiments in this paragraph up through the first embodiment in this paragraph further comprising separating the gaseous FCC hot product stream into the dilute ethylene stream, a C3 hydrocarbon stream, a C4 hydrocarbon stream, and a C5+ hydrocarbon stream. An embodiment of the disclosure is one, any or all of prior embodiments in this paragraph up through the first embodiment in this paragraph further comprising contacting the C4 hydrocarbon stream and the second hydrocarbon stream with the second stream of fluid catalyst in the second reactor riser to produce the second mixture of spent catalyst and product gases. An embodiment of the disclosure is one, any or all of prior embodiments in this paragraph up through the first embodiment in this paragraph further comprising contacting the C5+ hydrocarbon stream and the first hydrocarbon stream with the first stream of fluid catalyst in the first reactor riser to produce the first mixture of spent catalyst and product gases. An embodiment of the disclosure is one, any or all of prior embodiments in this paragraph up through the first embodiment in this paragraph wherein the first hydrocarbon stream is isoparaffin rich and the second hydrocarbon stream is more olefinic than the first hydrocarbon stream.

A second embodiment of the disclosure is a process for catalytic production of olefins comprising contacting a first hydrocarbon stream and a first stream of fluid catalyst in a first reactor riser to produce a first mixture of spent catalyst and product gases; separating the first mixture of spent catalyst and product gases to provide a first cracked product stream and a first stream of cool catalyst; separating the gaseous FCC hot product stream into a dilute ethylene stream, a C3 hydrocarbon stream, a C4 hydrocarbon stream, and a C5+ hydrocarbon stream; oligomerizing the dilute ethylene stream to produce a second hydrocarbon stream comprising C4+ oligomers; and contacting the second hydrocarbon stream with a second stream of fluid catalyst in a second reactor riser to produce a second mixture of spent catalyst and product gases. An embodiment of the disclosure is one, any or all of prior embodiments in this paragraph up through the second embodiment in this paragraph further comprising separating the first mixture of spent catalyst and product gases, in a first disengagement vessel, to provide the first cracked product stream and the first stream of cool catalyst and the second mixture of spent catalyst and product gases, in a second disengagement vessel, to provide a second cracked product stream and a second stream of cool catalyst. An embodiment of the disclosure is one, any or all of prior embodiments in this paragraph up through the second embodiment in this paragraph further comprising passing the first cracked product stream along with the second cracked product stream upwardly through a gas recovery conduit, and further separating from catalyst in a series of cyclones to produce a hot product stream. An embodiment of the disclosure is one, any or all of prior embodiments in this paragraph up through the second embodiment in this paragraph further comprising passing a n-paraffin rich stream to an isomerization unit to provide a first hydrocarbon stream rich in iso-paraffins. An embodiment of the disclosure is one, any or all of prior embodiments in this paragraph up through the second embodiment in this paragraph wherein oligomerizing the dilute ethylene stream to produce an oligomerization stream and separating the oligomerization stream into a C2− light gases stream and the second hydrocarbon stream comprising C4+ oligomers. An embodiment of the disclosure is one, any or all of prior embodiments in this paragraph up through the second embodiment in this paragraph wherein the first hydrocarbon stream is isoparaffin rich and the second hydrocarbon stream is more olefinic than the first hydrocarbon stream. An embodiment of the disclosure is one, any or all of prior embodiments in this paragraph up through the second embodiment in this paragraph further comprising contacting the C4 hydrocarbon stream and the second hydrocarbon stream with the second stream of fluid catalyst in the second reactor riser to produce the second mixture of spent catalyst and product gases.

A third embodiment of the disclosure is a process for catalytic production of olefins comprising passing a n-paraffin rich stream to an isomerization unit to provide a first hydrocarbon stream rich in iso-paraffins; contacting the first hydrocarbon stream with a first stream of fluid catalyst in a first reactor riser to produce a first mixture of spent catalyst and product gases; separating, in a first disengagement vessel, the first mixture of spent catalyst and product gases to provide a first cracked product stream and a first stream of cool catalyst; separating a dilute ethylene stream from the first cracked product stream; oligomerizing olefins in the dilute ethylene stream to produce a second hydrocarbon stream comprising C4+ oligomers; and contacting the second hydrocarbon stream with a second stream of fluid catalyst in a second reactor riser to produce a second mixture of spent catalyst and product gases. An embodiment of the disclosure is one, any or all of prior embodiments in this paragraph up through the third embodiment in this paragraph further comprising separating, in a second disengagement vessel, the second mixture of spent catalyst and product gases to provide a second cracked product stream and a second stream of cool catalyst. An embodiment of the disclosure is one, any or all of prior embodiments in this paragraph up through the third embodiment in this paragraph further comprising passing the first cracked product stream along with the second cracked product stream upwardly through a gas recovery conduit, and further separating from catalyst in a series of cyclones to produce a hot product stream. An embodiment of the disclosure is one, any or all of prior embodiments in this paragraph up through the third embodiment in this paragraph further comprising separating the dilute ethylene stream from the hot product stream. An embodiment of the disclosure is one, any or all of prior embodiments in this paragraph up through the third embodiment in this paragraph wherein the second reactor riser operates at a lower outlet temperature and/or a different catalyst density than the first reactor riser. An embodiment of the disclosure is one, any or all of prior embodiments in this paragraph up through the third embodiment in this paragraph wherein the first hydrocarbon stream has more than 60 wt % iso-paraffins, and second hydrocarbon stream has more than 40 wt % olefins.

Without further elaboration, it is believed that using the preceding description that one skilled in the art can utilize the present disclosure to its fullest extent and easily ascertain the essential characteristics of this disclosure, without departing from the spirit and scope thereof, to make various changes and modifications of the disclosure and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process for catalytic production of olefins comprising:

passing a feed stream to an isomerization unit to provide a first hydrocarbon stream rich in iso-paraffins;

contacting a first hydrocarbon stream with a first stream of fluid catalyst in a first reactor riser to produce a first mixture of spent catalyst and product gases;

separating the first mixture of spent catalyst and product gases into a first cracked product stream and a first stream of cool catalyst;

separating a dilute ethylene stream from said first cracked product stream;

oligomerizing said dilute ethylene stream to produce a second hydrocarbon stream comprising $C_4$+ oligomers; and contacting said second hydrocarbon stream with a second stream of fluid catalyst in a second reactor riser to produce a second mixture of spent catalyst and product gases.

2. The process of claim 1 wherein the first mixture of spent catalyst and product gases are separated in a first disengagement vessel and further comprising separating, in a second disengagement vessel, the second mixture of spent catalyst and product gases to provide a second cracked product stream and a second stream of cool catalyst.

3. The process of claim 2 further comprising passing said first cracked product stream along with said second cracked product stream upwardly through a gas recovery conduit, and further separating from catalyst in a series of cyclones to produce a gaseous FCC hot product stream.

4. The process of claim 3 further comprising separating said gaseous FCC hot product stream into said dilute ethylene stream, a $C_3$ hydrocarbon stream, a $C_4$ hydrocarbon stream, and a $C_5$+ hydrocarbon stream.

5. The process of claim 4 further comprising contacting said $C_4$ hydrocarbon stream and said second hydrocarbon stream with said second stream of fluid catalyst in said second reactor riser to produce said second mixture of spent catalyst and product gases.

6. The process of claim 4 further comprising contacting said $C_5$+ hydrocarbon stream and said first hydrocarbon stream with said first stream of fluid catalyst in said first reactor riser to produce said first mixture of spent catalyst and product gases.

7. The process of claim 1 wherein said first hydrocarbon stream is isoparaffin rich and said second hydrocarbon stream is more olefinic than said first hydrocarbon stream.

8. A process for catalytic production of olefins comprising:

contacting a first hydrocarbon stream and a first stream of fluid catalyst in a first reactor riser to produce a first mixture of spent catalyst and product gases;

separating the first mixture of spent catalyst and product gases to provide a first cracked product stream and a first stream of cool catalyst;

separating said first cracked product stream into a dilute ethylene stream, a $C_3$ hydrocarbon stream, a $C_4$ hydrocarbon stream, and a $C_5$+ hydrocarbon stream;

oligomerizing said dilute ethylene stream to produce a second hydrocarbon stream comprising $C_4$+ oligomers; and contacting said second hydrocarbon stream with a second stream of fluid catalyst in a second reactor riser to produce a second mixture of spent catalyst and product gases.

9. The process of claim 8 further comprising separating the first mixture of spent catalyst and product gases, in a first disengagement vessel, to provide said first cracked product stream and said first stream of cool catalyst and the second mixture of spent catalyst and product gases, in a second disengagement vessel, to provide a second cracked product stream and a second stream of cool catalyst.

10. The process of claim 9 further comprising passing said first cracked product stream along with said second cracked product stream upwardly through a gas recovery conduit, and further separating from catalyst in a series of cyclones to produce a hot product stream.

11. The process of claim 8 further comprising passing a n-paraffin rich stream to an isomerization unit to provide the first hydrocarbon stream rich in iso-paraffins.

12. The process of claim 8 wherein oligomerizing said dilute ethylene stream to produce an oligomerization stream and separating said oligomerization stream into a $C_2$− light gases stream and said second hydrocarbon stream comprising $C_4$+ oligomers.

13. The process of claim 8 wherein said first hydrocarbon stream is isoparaffin rich and said second hydrocarbon stream is more olefinic than said first hydrocarbon stream.

14. The process of claim 13 further comprising contacting said $C_4$ hydrocarbon stream and said second hydrocarbon stream with said second stream of fluid catalyst in said second reactor riser to produce said second mixture of spent catalyst and product gases.

15. A process for catalytic production of olefins comprising:

passing a n-paraffin rich stream to an isomerization unit to provide a first hydrocarbon stream rich in iso-paraffins;

contacting said first hydrocarbon stream with a first stream of fluid catalyst in a first reactor riser to produce a first mixture of spent catalyst and product gases;

separating, in a first disengagement vessel, the first mixture of spent catalyst and product gases to provide a first cracked product stream and a first stream of cool catalyst;

separating a dilute ethylene stream from said first cracked product stream;

oligomerizing olefins in said dilute ethylene stream to produce a second hydrocarbon stream comprising $C_4$+ oligomers; and contacting said second hydrocarbon stream with a second stream of fluid catalyst in a second reactor riser to produce a second mixture of spent catalyst and product gases.

16. The process of claim 15 further comprising separating, in a second disengagement vessel, the second mixture of spent catalyst and product gases to provide a second cracked product stream and a second stream of cool catalyst.

17. The process of claim 16 further comprising passing said first cracked product stream along with said second cracked product stream upwardly through a gas recovery conduit, and further separating from catalyst in a series of cyclones to produce a hot product stream.

18. The process of claim 17 further comprising separating said dilute ethylene stream from said hot product stream.

19. The process of claim 15 wherein said second reactor riser operates at a lower outlet temperature and/or a different catalyst density than said first reactor riser.

20. The process of claim 15 wherein the first hydrocarbon stream has more than 60 wt % iso-paraffins, and second hydrocarbon stream has more than 40 wt % olefins.

* * * * *